(12) United States Patent
Piantoni et al.

(10) Patent No.: US 10,213,346 B2
(45) Date of Patent: Feb. 26, 2019

(54) UNIT FOR FORMING ABSORBENT SANITARY ARTICLES AND METHOD FOR MAKING ABSORBENT SANITARY ARTICLES

(71) Applicant: GDM S.p.A., Bologna (IT)

(72) Inventors: Matteo Piantoni, Albino (IT); Valerio Soli, Bologna (IT)

(73) Assignee: GDM S.p.A., Bologna (IT)

(*) Notice: Subject to any disclaimer, the term of this patent is extended or adjusted under 35 U.S.C. 154(b) by 0 days.

(21) Appl. No.: 15/569,048

(22) PCT Filed: May 2, 2016

(86) PCT No.: PCT/IB2016/052479
§ 371 (c)(1),
(2) Date: Oct. 24, 2017

(87) PCT Pub. No.: WO2016/178128
PCT Pub. Date: Nov. 10, 2016

(65) Prior Publication Data
US 2018/0133069 A1    May 17, 2018

(30) Foreign Application Priority Data
May 4, 2015 (IT) .............................. BO2015A0221

(51) Int. Cl.
*B32B 37/00* (2006.01)
*A61F 13/15* (2006.01)
(Continued)

(52) U.S. Cl.
CPC .. *A61F 13/15739* (2013.01); *A61F 13/15723* (2013.01); *A61F 13/15764* (2013.01);
(Continued)

(58) Field of Classification Search
CPC .......... A61F 13/15723; A61F 13/15739; A61F 13/15764; B29C 65/08; B29C 65/083
(Continued)

(56) References Cited

U.S. PATENT DOCUMENTS

| 5,660,679 A * | 8/1997 | Rajala ............... B29C 66/81463 156/580.1 |
| 9,333,705 B1 * | 5/2016 | Fujita ................ B29C 66/72343 |

(Continued)

FOREIGN PATENT DOCUMENTS

| EP | 2796271 A1 | 10/2014 |
| WO | WO2014188302 A1 | 11/2014 |

OTHER PUBLICATIONS

International Search Report and Written Opinion dated Aug. 1, 2016 from counterpart PCT App No. PCT/IB2016/052479.

*Primary Examiner* — James D Sells
(74) *Attorney, Agent, or Firm* — Shuttleworth & Ingersoll, PLC; Timothy Klima

(57) ABSTRACT

A unit for forming absorbent sanitary articles including a drum rotatable about its axis of rotation and having a circumferential peripheral surface movable along a feed direction, first feeding means for feeding a succession of pairs of panels of material facing the circumferential peripheral surface and configured to position each pair in such a way that the respective two panels are facing each other and transversely aligned with the feed direction and second feeding means for feeding a continuous web of material suitable for defining at least part of the main body of an absorbent sanitary article, and configured to position the web on the circumferential peripheral surface of the drum in such a way that each panel projects partly sideways from the web. The unit comprises an ultrasonic sealing station located along the circumferential peripheral surface of the drum, in a zone located operatively downstream of the second feed- (Continued)

ing means, and configured to attach each panel of the pair to the web at at least one plurality of sealing points arranged in succession along the feed direction.

8 Claims, 2 Drawing Sheets

(51) Int. Cl.
    *B29C 65/08*     (2006.01)
    *B29C 65/78*     (2006.01)
    *B29L 31/48*     (2006.01)
    *B29C 65/00*     (2006.01)

(52) U.S. Cl.
    CPC ............ *B29C 65/08* (2013.01); *B29C 65/083* (2013.01); *A61F 2013/15869* (2013.01); *B29C 65/086* (2013.01); *B29C 65/7847* (2013.01); *B29C 65/7888* (2013.01); *B29C 66/1122* (2013.01); *B29C 66/21* (2013.01); *B29C 66/472* (2013.01); *B29C 66/8169* (2013.01); *B29C 66/81465* (2013.01); *B29C 66/83415* (2013.01); *B29C 66/83417* (2013.01); *B29C 66/8432* (2013.01); *B29C 66/84121* (2013.01); *B29L 2031/4878* (2013.01)

(58) Field of Classification Search
    USPC ...................................................... 156/580.1
    See application file for complete search history.

(56) References Cited

U.S. PATENT DOCUMENTS

| | | | |
|---|---|---|---|
| 9,452,565 B2 * | 9/2016 | Fujita | ................ B29C 66/8412 |
| 2007/0251643 A1 * | 11/2007 | Umebayashi | ..... A61F 13/15739 |
| | | | 156/350 |
| 2013/0037201 A1 | 2/2013 | Pagel et al. | |

* cited by examiner

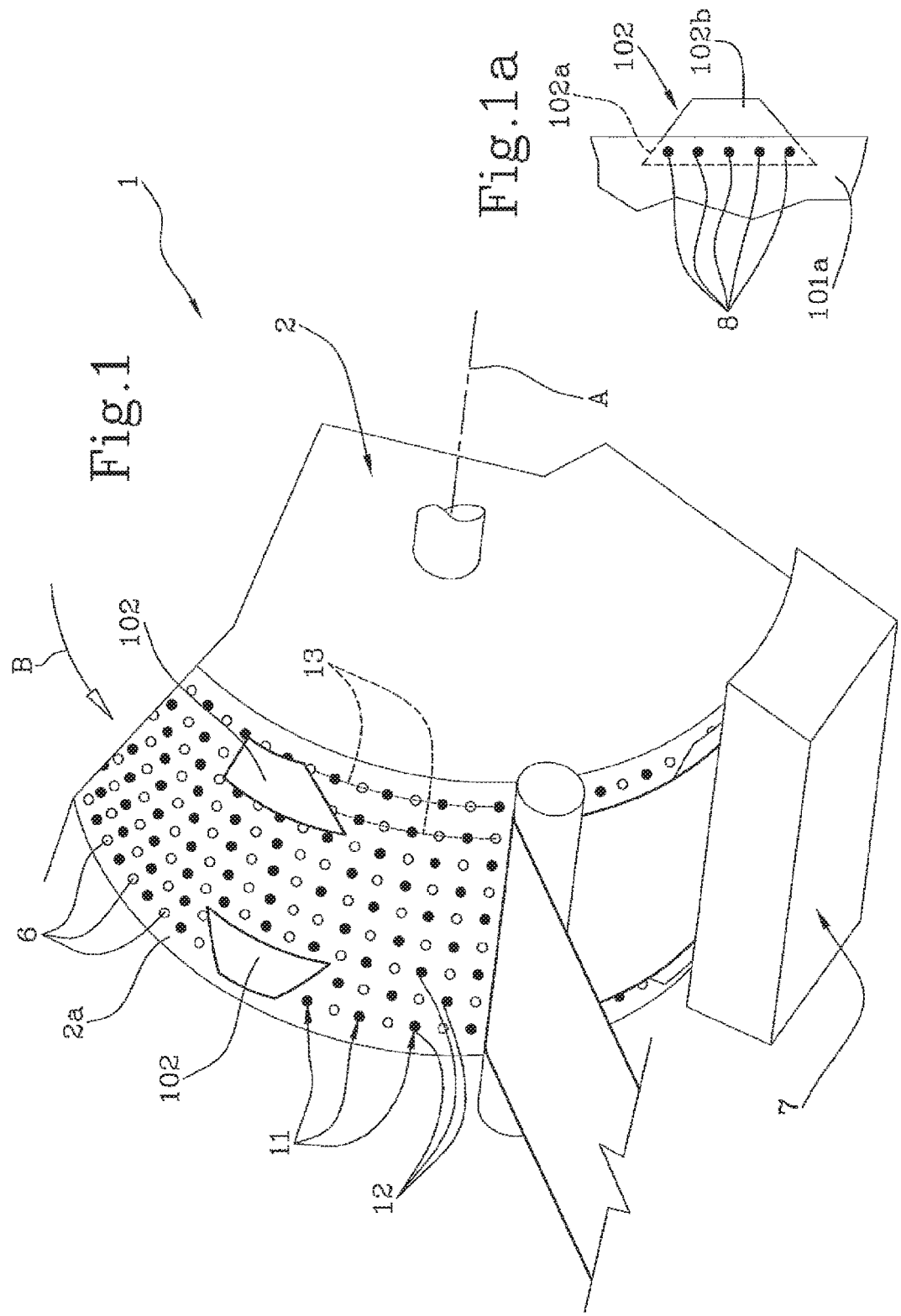

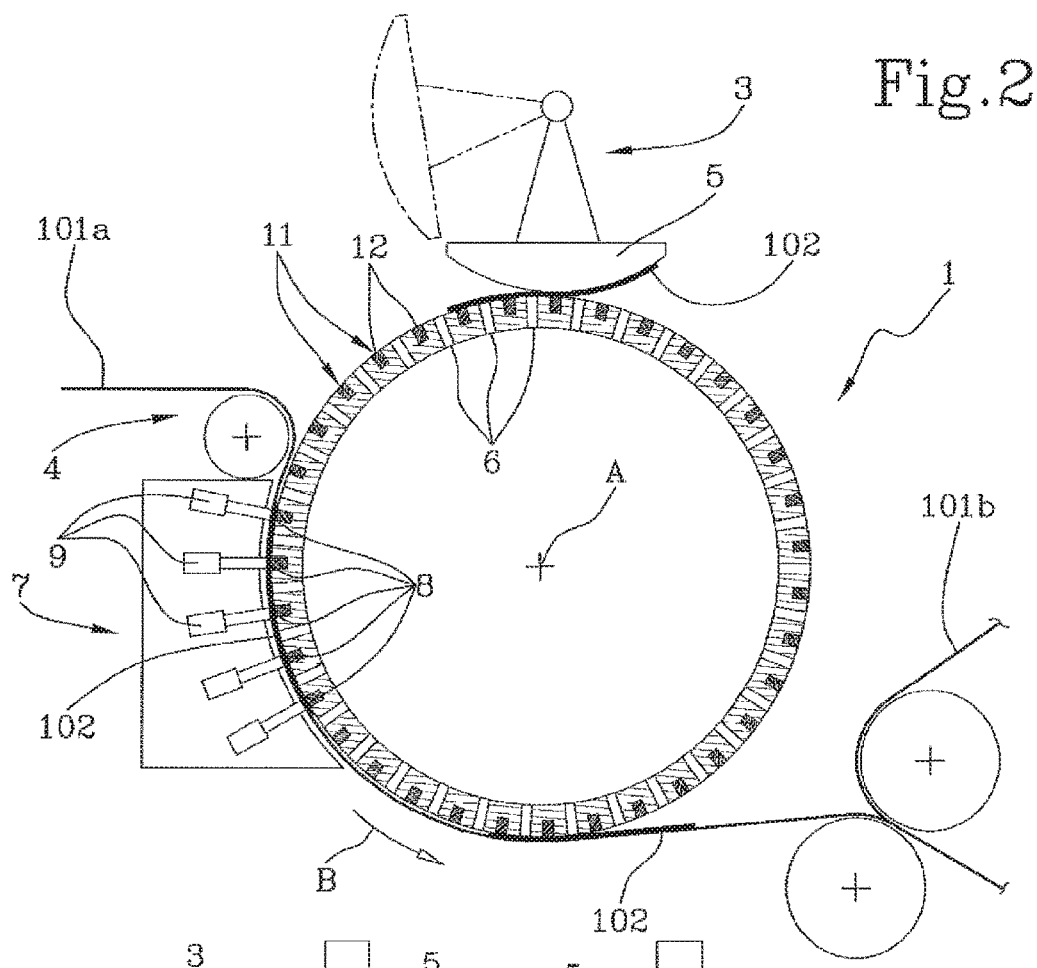
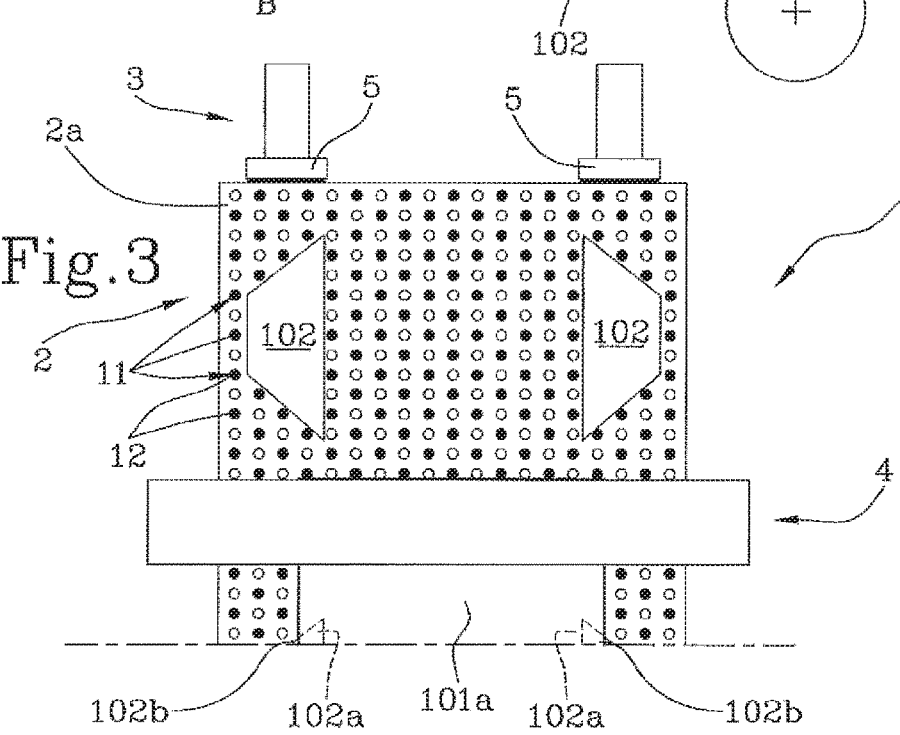

UNIT FOR FORMING ABSORBENT SANITARY ARTICLES AND METHOD FOR MAKING ABSORBENT SANITARY ARTICLES

This application is the National Phase of International Application PCT/IB2016/052479 filed May 2, 2016 which designated the U.S.

This application claims priority to Italian Patent Application No. BO2015A000221 filed May 4, 2015, which application is incorporated by reference herein.

TECHNICAL FIELD

This invention relates to a unit for forming absorbent sanitary articles and to a method for making absorbent sanitary articles.

The invention is therefore applicable in particular to the sector of automatic machines, and in particular for the production of absorbent sanitary articles such as disposable nappies for children or adults.

BACKGROUND ART

In absorbent articles of known type, the main body of the article has a front end portion, also referred to simply as "front" in the jargon of the trade and which, in use, as this implies, covers a front part of the wearer's body, and a back end portion, also referred to simply as "back" in the jargon of the trade and which, in use, as this implies, covers a back part of the wearer's body.

These articles comprise a pair of panels or side wings, which may, if necessary, consist of two or more connected parts, which extend from opposite sides of the front end portion and which are called "front panels" in the jargon of the trade, and a pair of panels or side wings, which may, if necessary, consist of two or more connected parts, which extend from opposite sides of the back end portion and which are called "back panels" in the jargon of the trade.

This invention is applicable in the stations for assembling the absorbent sanitary article, where the panels, or wings, are applied to the main body, and that is to say, to a continuous web which, when the product is finished, defines the "top sheet" (permeable layer) or the "back sheet" (impermeable layer) of the main body, or "chassis", of the article.

In the prior art, units for forming the absorbent article are defined by a drum with which are associated means for feeding a succession of pairs of panels, or wings, and means for feeding at least one continuous web of material.

In some embodiments, the means for feeding the succession of pairs are subdivided into two wheels, or arms, each configured to apply pairs of front or back panels, typically differing in shape and composition.

Whatever the case, prior art units generally comprise an adhesive applicator unit configured to apply a predetermined quantity of adhesive on the panels or on the web at a panel coupling zone.

More specifically, this unit is configured to release enough adhesive to position the panel "provisionally" but not to fix it permanently.

In effect, prior art units are provided with a sealing station located downstream of the drum and equipped with a plurality of sonotrodes facing an abutment surface (or anvil) where the panels, positioned by means of the adhesive, are fixed securely to the web at two or more points.

Disadvantageously, the presence of an adhesive applicator unit introduces several critical factors and complications in the machine.

In effect, the ultrasonic sealing station, located after the adhesive applicator unit, tends to overheat the adhesive, melting it and causing it to seep into the absorbent article.

Moreover, the melted adhesive does not affect only the absorbent article but tends to contaminate the sealing station as a whole, especially the sonotrode, or anvil, thus increasing maintenance costs and machine down times.

DISCLOSURE OF THE INVENTION

In light of the above, this invention has for an aim to provide a unit for forming absorbent sanitary articles and a method for making absorbent sanitary articles which can overcome the above mentioned drawbacks of the prior art.

More specifically, this invention has for an aim to provide a unit for forming absorbent sanitary articles and a reliable method for making absorbent sanitary articles which can increase the quality of the products.

Another aim of the invention is to provide a unit for forming absorbent sanitary articles which is compact and reliable.

These aims are achieved by a unit for forming absorbent sanitary articles having features as disclosed herein, as well as by a method for making absorbent sanitary articles having features as disclosed herein.

More specifically the unit according to this invention comprises a drum rotatable about its axis of rotation and having a circumferential peripheral surface movable along a feed direction, first feeding means for feeding a succession of pairs of panels of material facing the circumferential peripheral surface and configured to position each pair in such a way that the respective two panels are facing each other and are transversely aligned with the feed direction and second feeding means for feeding a continuous web of material suitable for defining at least part of the main body of an absorbent sanitary article, and configured to position the web on the circumferential peripheral surface of the drum in such a way that each panel projects partly sideways from the web.

According to one aspect of the invention, the unit comprises an ultrasonic sealing station located along the circumferential peripheral surface of the drum, in a zone located operatively downstream of the feeding means for feeding the web and configured to attach each panel of the pair to the web at at least one plurality of sealing points arranged in succession along the feed direction.

Advantageously, the panel, or wing, is thus connected to the web along its full length directly on the drum and without the aid of positioning adhesives, thus fulfilling the aims of the invention.

More specifically, the drum meets the need to place the panels in the correct position by means of a plurality of suction cavities simultaneously with the need to seal, that is to say, to fix, the panels on the web without the aid of an adhesive.

In effect, the unit comprises, immediately downstream of the drum, without any other sealing station in between, an applicator station for applying an absorbent core to the web and/or an applicator station for applying a further continuous web to the continuous web so that the panels are interposed between the continuous web and the further continuous web.

It should be noted that the ultrasonic sealing station preferably comprises at least one first sonotrode and at least one second sonotrode facing the circumferential peripheral surface of the drum and spaced from each other transversely to the feed direction in such a way that each acts on a respective panel of each pair.

Thus, it is the drum itself which acts as an anvil for the sonotrode or the sonotrodes of the sealing station.

In accordance with the foregoing, the method according to the invention comprises a step of feeding a succession of pairs of panels, a step of feeding a continuous web of material suitable for defining at least part of the main body of an absorbent sanitary article (preferably non-woven fabric), a step of placing each pair on a peripheral surface of a rotatable drum in such a way that the respective two panels are facing each other and transversely aligned with a feed direction, and a step of positioning the web on the circumferential peripheral surface of the drum in such a way that each panel projects partly sideways from the web.

The method also comprises a step of sealing the panels to the web using ultrasound, where sealing is performed on the drum by making a plurality of sealing points arranged in succession along the feed direction.

BRIEF DESCRIPTION OF THE DRAWINGS

These and other features and advantages of the invention will become more apparent from the following exemplary, and hence non limiting, description of a preferred, and hence non-exclusive, embodiment of a unit for forming absorbent sanitary articles and of a method for making absorbent sanitary articles, as illustrated in the accompanying drawings, in which:

FIG. 1 is a schematic perspective view of a unit for forming absorbent sanitary articles according to this invention;

FIG. 2 shows a schematic front view of the unit for forming absorbent sanitary articles of FIG. 1;

FIG. 3 shows a schematic side view of the unit for forming absorbent sanitary articles of FIG. 1.

DETAILED DESCRIPTION OF PREFERRED EMBODIMENTS OF THE INVENTION

With reference to the accompanying drawings, the numeral 1 denotes a unit for forming absorbent sanitary articles 100 according to the invention.

The forming unit 1 is located along a line for the production of absorbent sanitary articles, such as nappies or incontinence underwear, having a main portion, or "chassis", provided with an absorbent core and one or more auxiliary elements defined, preferably, by panels 102 or side wings.

More precisely, each absorbent sanitary article 100 comprises a main body 101, or chassis, extending along a respective axis from a front end portion which, in use, will be placed at the front of the wearer, to a back end portion which, in use, will be placed at the back of the wearer, when the nappy is folded in a U shape around the wearer's crotch.

More specifically, the main body 101 of each absorbent article 100 is a composite item comprising at least one internal absorbent pad, normally made from cellulose fibres or SAP, placed inside a soft container defined, on one side, by a permeable sheet of non-woven fabric, or "top sheet", and on the other side, by an impermeable sheet (not illustrated) of polyethylene, or "back sheet".

The absorbent article 100 is also usually provided with a pair of front panels 102, or wings, extending sideways from the front end portion, and a pair of back panels 102, or wings, with reference to the nappy when worn by the user.

The front and back panels, usually different from each other, are made in such a way as to engage each other, to encircle the wearer's waist and, in use, to keep the nappy correctly in place.

The forming unit 1 is then provided with at least one drum 2 which is rotatable about a respective axis of rotation "A" and to which are associated first feeding means 3 for feeding (and applying) a succession of pairs of panels 102 and second feeding means 4 for feeding a continuous web 101a of material suitable for defining at least part of the main body 101.

More precisely, the drum 2 has a circumferential peripheral surface 2a which is movable along the feed direction "B" around the axis "A".

The first feeding means 3 are configured to apply on the drum 2, in particular on the circumferential peripheral surface 2a thereof, a succession of pairs of panels 102, or wings, defining the front pairs of panels and/or the rear pairs of panels.

It should be noted that the panels 102 are positioned in such a way that the panels in each pair are spaced from, and aligned with, each other transversely, that is at right angles, to a feed direction "B".

Preferably, therefore, the first feeding means 3 have a rotatable member 5 provided with at least one release portion substantially tangent to the drum 2 and preferably dimensioned to receive both of the panels 102 of each pair.

The second feeding means 4, on the other hand, are configured to apply the continuous web 101a on the drum 2, in particular on the circumferential peripheral surface 2a thereof.

More specifically, the second feeding means 4 are configured to feed the web 101a along a feed path "P" having a partly circular stretch around the drum 2.

Preferably, the stretch "T" of the feed path "P" occupies a circular sector covering an angle greater than 10°, and more preferably, of at least 20°.

The second feed means 4 are preferably located operatively downstream of the first feeding means 3. The second feeding means 4 are thus configured to place the web 101a on the drum 2 in such a way that the panels 102 are interposed between the web 101a itself and the circumferential peripheral surface 2a of the drum 2.

More precisely, the first feeding means 3 and the second feeding means 4 are configured in such a way that each panel 102 of each pair protrudes sideways from a respective longitudinal edge of the continuous web 101a.

Thus, after being applied to the web 101a, each panel 102 has an inner portion 102a which is joined to the web 101a and an outer portion 102b which projects sideways from the web 101a.

It should be noted that the first feeding means 3 may be located upstream of the second feeding means 4 (preferable) but, in some embodiments, also downstream of them.

To hold the panels 102 in place, the circumferential peripheral surface 2a of the drum 2 preferably has suction applied to it.

In other words, the drum 2 has, along its circumferential peripheral surface 2a, a plurality of suction cavities 6 arranged in succession along an at least partly circumferential direction.

The cavities are thus in fluid connection with vacuum generating means (not illustrated) for holding the panels 102 in place.

According to one aspect of the invention, the unit 1 comprises an ultrasonic sealing station 7 located along the circumferential peripheral surface 2a of the drum 2, in a zone located operatively downstream of the second feeding means 4.

In the preferred embodiment, the sealing station is located at the stretch "T".

The sealing station 7 is configured to attach each panel 102 of the pair to the web 101a at at least one plurality of sealing points 8 arranged in succession along the feed direction B.

It should be noted that the sealing station 7 seals the panel 102 to the web 101a permanently and that no further connecting stations are required.

In effect, in order to attach the wing 102a to the web 101a, the sealing station 7 is configured to operate on the inner portion of the wing at a plurality of points arranged in succession.

The suction cavities 6, on the other hand, operate on the outer portion 102b of the panels 102 during (and also before and after) sealing.

In this regard, the ultrasonic sealing station 7 comprises at least one first sonotrode 9 and at least one second sonotrode 10 facing the circumferential peripheral surface 2a of the drum 2 and spaced from each other transversely to the feed direction "B" in such a way that each acts on a respective panel 102 of each pair.

More precisely, the ultrasonic sealing station 7 comprises a plurality of first sonotrodes 9 and a plurality of second sonotrodes 10 configured to seal each panel 102 to the continuous web 101a at a corresponding plurality of points 8 arranged in succession along the feed direction "B".

Advantageously, this makes it possible to avoid the need to use pre-positioning adhesives or a plurality of sealing stations, making the structure of the unit 1 very compact and located entirely around the single drum 2.

It should be noted that, preferably, the first sonotrode (or sonotrodes) 9 and the second sonotrode (or sonotrodes) 10 are movable towards and away from each other in order to adapt to the size of the absorbent article 100.

In other words, the sealing station 7 is equipped with movement means (not illustrated) associated with the first sonotrode 9 and/or the second sonotrode 10 and configured to move them towards and away from each other.

Preferably, the movement means are operatively associated with a drive device and/or a control unit configured to define the position of the sonotrodes 9, 10 as a function of the size of the absorbent article 100 or of the panels 102.

Advantageously, that makes the forming unit 1 versatile and easy to adapt to size changeovers, which translates as significant savings of time and money for the manufacturer.

To allow ultrasonic sealing to be carried out, the circumferential peripheral surface 2a of the drum 2 defines an anvil 11 for the sonotrodes 9, 10.

For this purpose, the drum 2 has, along its circumferential peripheral surface 2a, a plurality of stops or abutments 12 defining respective anvils 11 for the sonotrodes 9, 10 and distributed along an at least partly circumferential direction.

Preferably, the stops 12 are defined by plates located in specific cavities made on the circumferential peripheral surface 2a of the drum 2.

These plates are made of a suitable material.

Thus, the drum 2 comprises a plurality of stops 12 located in circumferential succession along the circumferential peripheral surface 2a.

Preferably, the drum 2 comprises at least two substantially circumferential rows 13 of stops 12 in order to allow both panels 102 of each pair to be sealed in sequence.

In the preferred embodiment, the suction cavities 6 being arranged in axial and/or circumferential alternation with the stops 12, or abutments.

In other words, along the circumferential direction, the circumferential peripheral surface 2a is provided with suction cavities 6 alternated with stops 12 in order to combine maximum productivity with positioning precision.

Further, the circumferential peripheral surface 2a is preferably provided with suction cavities 6 alternated with stops 12 along an axial direction (parallel to the axis of rotation "A").

In other words, in the preferred embodiment, the circumferential peripheral surface 2a has a distributed pattern of suction cavities 6 and stops 12 in order to guarantee maximum versatility and positioning precision.

In effect, the distribution of suction cavities 6 along the entire circumferential peripheral surface 2a allows the panels to be correctly positioned independently of their shape and size, whilst the distribution of the stops 12 allows correct sealing to be carried out at several points whatever the position adopted by the sonotrodes 9, 10.

In a first embodiment, the unit 1 comprises an applicator station, located immediately downstream of the drum 2, for applying an absorbent core on the web 101a.

Alternatively, the unit 1 comprises an applicator station, located immediately downstream of the drum 2, for applying a further continuous web 101b to the continuous web 101a so that the panels are interposed between the continuous web 101a and the further continuous web 101b.

Thus, no further sealing station is provided and the positioning of the panels 102 is completed in the sealing station 7.

Advantageously, the forming unit 1 according to the invention is extremely compact and easy to maintain.

In effect, all the devices involved, such as the first and second feeding means 3 and 4 and the sealing station 7 are close and tangent to the circumferential peripheral surface 2a of the drum.

The unit 1 is thus configured to implement a method, also an object of the invention, for forming the absorbent sanitary article 100.

The method comprises a step of feeding a succession of pairs of panels 102 of material.

The panels 102 are made of a preferably elastic material to define the side wings for closing the absorbent article 100.

There is also a step of feeding a continuous web 101a of material suitable for defining at least part of the main body 101 of an absorbent sanitary article 100.

Preferably, the continuous web 101a is the top sheet of the main portion of the article. Hence, the web 101a is preferably made of non-woven fabric.

Alternatively, the web might be the back sheet of the article 100, in which case it would be made of a substantially impermeable material.

Preferably, therefore, each pair of panels 102 is placed on the peripheral surface 2a of a rotatable drum 2 in such a way that the respective two panels 102 are facing each other and transversely aligned with a feed direction "B".

Thus, the two panels 102 of each pair are aligned along an axial direction parallel to an axis of rotation of the drum 2 and spaced from each other by a predetermined quantity.

Next, or previously, the web 101a is positioned on the circumferential peripheral surface 2a of the drum 2 in such a way that each panel 102 projects partly sideways from the web 101a.

Thus, after positioning the panels 102 and the web 101a, each panel 102 has an inner portion 102a which is joined to/superposed on the web 101a and an outer portion 102b which projects sideways therefrom.

According to the invention, the method further comprises a step of ultrasonically sealing the panels 102, or rather the inner portion 102a thereof, to the web 101.

More specifically, the sealing step is performed on the drum 2 by making a plurality of sealing points 8 arranged in succession along the feed direction "B".

Simultaneously with the sealing step, there is a step of holding down the panels 102 by suction in order to keep the panels 102 properly in place while they are being sealed to the continuous web 101a.

Preferably, the step of holding down by suction starts before the sealing step and, more preferably, continues after the sealing step.

Advantageously, that way, the positioning of the panels 102 and of the web 101a remains constant and precise.

The sealing of the panels 102 to the web 101 is carried out entirely on the drum 2.

In light of this, the method comprises, immediately after the sealing step and without any other steps in between, a step of applying an absorbent core on the web 101a.

Alternatively, there may be a step applying a further continuous web 101b to the continuous web 101a so that the panels 102 are interposed between the continuous web 101a and the further continuous web 101b.

The invention achieves the preset aims and brings important advantages.

In effect, the provision of an ultrasonic sealing station along the forming drum makes it possible to attach the panels to the web permanently and thus to significantly increase the quality of the products (without adhesive) and at the same time to reduce machine production costs/downtime.

Moreover, the provision of a peripheral surface having a distributed pattern of suction openings and stops for the sonotrodes allows maximum versatility of use and minimizes setup times during changeovers.

The invention claimed is:

1. A unit for forming absorbent sanitary articles, comprising:
    a drum rotatable about an axis of rotation and having a circumferential peripheral surface movable along a feed direction;
    a first feeding device including a rotatable member for feeding a succession of pairs of panels of material facing the circumferential peripheral surface and configured to position each pair such that two panels of each pair of panels are facing each other and transversely aligned with the feed direction;
    a second feeding device including a roller for feeding a continuous web of material suitable for defining at least part of a main body of an absorbent sanitary article, and configured to position the continuous web on the circumferential peripheral surface such that each of the two panels projects partly sideways from the continuous web;
    an ultrasonic sealing station located along the circumferential peripheral surface, in a zone located operatively downstream of the second feeding device, and configured to attach each of the two panels to the continuous web at at least one plurality of sealing points arranged in succession along the feed direction; the ultrasonic sealing station comprising at least one first sonotrode and at least one second sonotrode facing the circumferential peripheral surface and spaced from each other transversely to the feed direction such that each acts on a respective one of the two panels;
    wherein the at least one first sonotrode and the at least one second sonotrode are movable towards and away from each other in order to adapt to a size of the absorbent article.

2. The unit according to claim 1, wherein the at least one first sonotrode includes a plurality of first sonotrodes and the at least one second sonotrode includes a plurality of second sonotrodes configured to seal the respective one of the two panels to the continuous web at a corresponding plurality of points arranged in succession along the feed direction.

3. The unit according to claim 2, wherein the drum has, along the circumferential peripheral surface, a plurality of suction cavities arranged in succession along an at least partly circumferential direction and a plurality of stops, or abutments, defining respective anvils for the plurality of first sonotrodes and the plurality of second sonotrodes and distributed both along the at least partly circumferential direction and along an axial direction, with reference to the axis of rotation of the drum.

4. The unit according to claim 3, wherein the plurality of suction cavities are arranged in at least one chosen form axial and circumferential alternation with the plurality of stops, or abutments.

5. The unit according to claim 3, wherein the plurality of suction cavities are arranged both in axial and circumferential alternation with the plurality of stops, or abutments.

6. The unit according to claim 1, wherein the second feeding device is configured to feed the continuous web along a feed path having a partly circular stretch around the drum; the ultrasonic sealing station being located at the partly circular stretch.

7. The unit according to claim 6, wherein the partly circular stretch occupies a circular sector of at least 20°.

8. The unit according to claim 1, and further comprising, immediately downstream of the drum, at least one chosen from an applicator station for applying an absorbent core to the continuous web and an applicator station for applying a further continuous web to the continuous web so that the two panels are interposed between the continuous web and the further continuous web.

* * * * *